United States Patent [19]

Ueda

[11] Patent Number: 4,927,530

[45] Date of Patent: May 22, 1990

[54] APPARATUS FOR PROCESSING SLUDGE

[75] Inventor: Iwao Ueda, 416, Nanba-cho, Matsubara-sagaru, Nishikiyamachi-dori, Shimogyo-ku, Kyoto, Japan

[73] Assignees: Iwao Ueda; Chie Ueda; Etsuko Ueda, all of Japan

[21] Appl. No.: 187,634

[22] Filed: Apr. 28, 1988

[30] Foreign Application Priority Data

Apr. 30, 1987 [JP] Japan ............................ 62-107534

[51] Int. Cl.$^5$ ............................................. C02F 11/04
[52] U.S. Cl. .................................... 210/149; 210/177; 210/187; 210/207; 210/533
[58] Field of Search ................................ 210/177–180, 210/187, 742, 774, 96.1, 149, 207, 208, 258, 533

[56] References Cited

U.S. PATENT DOCUMENTS

| | | | |
|---|---|---|---|
| 3,255,887 | 6/1966 | Walker et al. | 210/187 |
| 3,981,803 | 9/1976 | Coulthard | 210/178 |
| 4,172,034 | 10/1979 | Carlsson et al. | 210/178 |
| 4,293,412 | 10/1981 | Lescure | 210/180 X |

OTHER PUBLICATIONS

Australian Patent Application 31432/84.

*Primary Examiner*—Tom Wyse
*Attorney, Agent, or Firm*—Lowe, Price, LeBlanc, Becker & Shur

[57] ABSTRACT

A sludge processing apparatus is provided that includes a processing tank, in which sludge flowing in through a sluge inflow pipe is deposited and processed, a submersible pump disposed in the center of bottom of the processing tank to take in the sludge laid on the bottom of the tank and spout it upward to a liquid surface, a circulation guide plate for circulating the sludge spouted by the submersible pump through the whole tank, a chemical feeder for feeding to the processing tank a selected chemical for promoting activity of anaerobic bacteria carrying out anaerobic digestion, a hot water pipe disposed in the vicinity of the bottom of the processing tank, a heating-and-circulating device for heating a heating medium and circulating it through the hot water pipe, temperature control means for controlling a temperature of sludge in the processing tank to be required value, and a drain pump for pumping supernatant water left after processing of the sludge out of the tank through a drain pipe. The method according to this invention combines the corresponding steps.

9 Claims, 2 Drawing Sheets

4,927,530

APPARATUS FOR PROCESSING SLUDGE

BACKGROUND OF THE INVENTION

1. Field of the Invention:

The present invention relates to apparatus and a method for processing excess sludge which is necessarily generated in and sent out of various sewage treatment plants as a result of processing of sewage water such as industrial effluent, discharges from homes or the like, using micro-organisms.

2. Background of the Prior Art:

The process of eliminating water polluting materials such as BOD, or COD contained in sewage water, by oxidatively decomposing them with micro-organisms, includes the activated sludge method, trickling filter method and the catalytic oxidation method. It is well known that excess sludge is produced according to the purification process and deposited on, for example, the bottom of a tank of the processing unit. If the excess sludge is left as it deposited, purification performance of the treating equipment is lowered, eventually resulting in incapability of the equipment. Accordingly, it is essential to remove the excess sludge out of the tank and process it.

Hitherto, there have been proposed several ways to process the deposited sludge, e.g., a method in which sludge is dewatered, dried and incinerated; a method in which dewatered sludege is buried under the ground or dumped into the ocean; a method in which dewatered sludge is made into compost to be effectively utilized as fertilizer, or a method in which sludge is quantitatively reduced by digestion with anaerobic bacteria, and others.

In the above known methods, however, there are serious drawbacks in that there is high equipment cost and also a fuel cost in the first method of dewatering, drying and incinerating the sludge. High transportation cost is incurred in the second method of burying the sludge under the ground because a large amount of sludge must be carried to the dumping site, and moreover it is rather difficult to get an extensive dumping site. Likewise, in the third method of dumping the sludge into the ocean, there is a drawback of transportation cost and moreover it raises the problem of ocean pollution. In the fourth method of utilizing the sludge by transforming it into compost, there is a drawback in that a high construction cost of processing facilities is required; and another drawback is that the utility of sludge transformed into the compost is lower than that of chemical fertilizer industrially produced.

On the other hand, in the method of reducing the quantity of sludge, utilizing digestion by anaerobic bacteria, processing equipment of rather simple construction can be used and its operation is also relatively simple, and therefore this method has been traditionally adopted in the typical sludge treatment process in sewage plants. In this method, however, it takes long for the sludge to be treated, e.g., over 6 to 8 months, because it is bacteria that carries out the treatment in the form of micro-biological decomposition. Accordingly, this method also results in a high construction cost for the treating equipment since a large scale processing facility is essential for the purpose of carrying out large-scale treatment. Moreover, during the period of digestion of sludge by the anaerobic bacteria, methane gas is continuously generated, and during the period of acidity reduction, large amount of offensive malodorous gases such as hydroxide, mercaptan, indole, etc. is generated. Accordingly, routine operation control of the processing facility is very important and troublesome. Besides, organic material of high concentration is contained in supernatant liquer left after the sludge treatment, and therefore a further problem exists in that some secondary process has to be applied to this supernatant liqueur.

SUMMARY OF THE INVENTION

The present invention was made to overcome the above-discussed drawbacks in the conventional method utilizing digestion of sludge by anaerobic bacteria and has an object of providing a sludge processing apparatus in which sludge processing can be efficiently carried out in a shorter period, the amount of generation of methane gas per unit time is increased in order to shorten the period of generation thereof, generation of offensive odor gas in the period of acidity reduction is restrained, and there is no generation of supernatant liqueur requiring a secondary disposal process.

In particular, the invention provides a sludge processing apparatus of simple construction adequate to be combined with a sewage water treatment equipment of relatively small scale, thereby achieving a sludge processing in which equipment cost and running cost are relatively reduced, and in which routine operation control is not troublesome.

The foregoing object is accomplished by providing a sludge processing apparatus that includes a processing tank in which sludge flowing in through a sludge inflow pipe is deposited and processed; a submersible pump which is disposed in the center of bottom of the processing tank for taking in the sludge laid on the bottom of the tank and spouting it upward to liquid surface; a circulation guide plate which circulates the sludge spouted by the submergible pump in the whole tank; a chemical feeder which feeds a chemical for promoting acitivity of anaerobic bacteria carrying out anaerobic digestion to the processing tank; a hot water pipe which is disposed in the vicinity of the bottom of the processing tank; a heating-and-circulating device which heats a heating medium and circulates it through the hot water pipe; temperature control means which controls a temperature of sludge in the processing tank to be a predetermined value; and a drain pump which pumps supernatant water left after processing the sludge out of the tank through a drain pipe.

In the sludge processing apparatus and method according to the present invention, sludge sent from sewage water treating equipment flows in the processing tank through the sludge inflow pipe, and the sludge thus entering the processing tank is held in the tank, and is subjected to circulation in the tank by a submersible pump and circulation guide plate. A selected chemical is fed to the sludge under the circulation, to be mixed with it stirring. While the sludge is circulating in the tank, a heating medium heated by a heating-and-circulating device is further heated by a hot water pipe arranged inside the tank, and the sludge is controlled by the temperature controller to have its optimum temperature for treatment whereby anaerobic bacteria living in the sludge is activated. By the vigorous activity of anaerobic bacteria, the anaerobic digestion of the sludge is speedily carried out, shortening thereby the cycle of acidic and alkaline fermentation which, in turn, shortens the period necessary for the processing. Thus, the amount of generation of methane gas per unit time is increased thereby shortening the period for such generation. Generation of offensive malodorous gas in the period of acidity reduction is thus significantly restrained. Further, only a deposit of inorganic material is left on the bottom of the processing tank after the processing. Because the chemical for promoting the activity of the bacteria is included in the supernatant water obtained after processing the sludge, it is preferred that the supernatant water containing the chemical is first pumped out by the drain pump through the drain pipe, and then fed back to the processing tank of the sludge processing apparatus to improve the sludge processing efficiency.

In effect, in the sludge processing apparatus of above construction and function according to the present invention, sludge processing can be carried out effciently in shorter period, and there is no need for a large-scale processing facility, which means that the sludge processing apparatus according to the invention is of simple construction and preferably combined with a sewage water treating equipment of rather small scale. As a result of this, equipment cost thereof is relatively low. The operating cost is also reduced because no fuel cost is required as in the conventional incinerating method. Furthermore, routine operational control is facilitated because the generation of methane gas according to the sludge processing takes places for only a short period, hence generation of offensive odor is restrained.

BRIEF DESCRIPTION OF THE DRAWINGS

Other objects, features and advantages of the present invention will become apparent in the course of the following description with the accompanying drawings wherein:

FIG. 1 is a partially sectional front view taken along the line I—I' in FIG. 2 to show schematically a construction of the sludge processing apparatus according to the present invention; and FIG. 2 is a sectional view of the construction taken along the line II—II' in FIG. 1.

DESCRIPTION OF THE PREFERRED EMBODIMENT

Described herainafter with reference to the drawings is a preferred embodiment of the invention.

Figure 1:
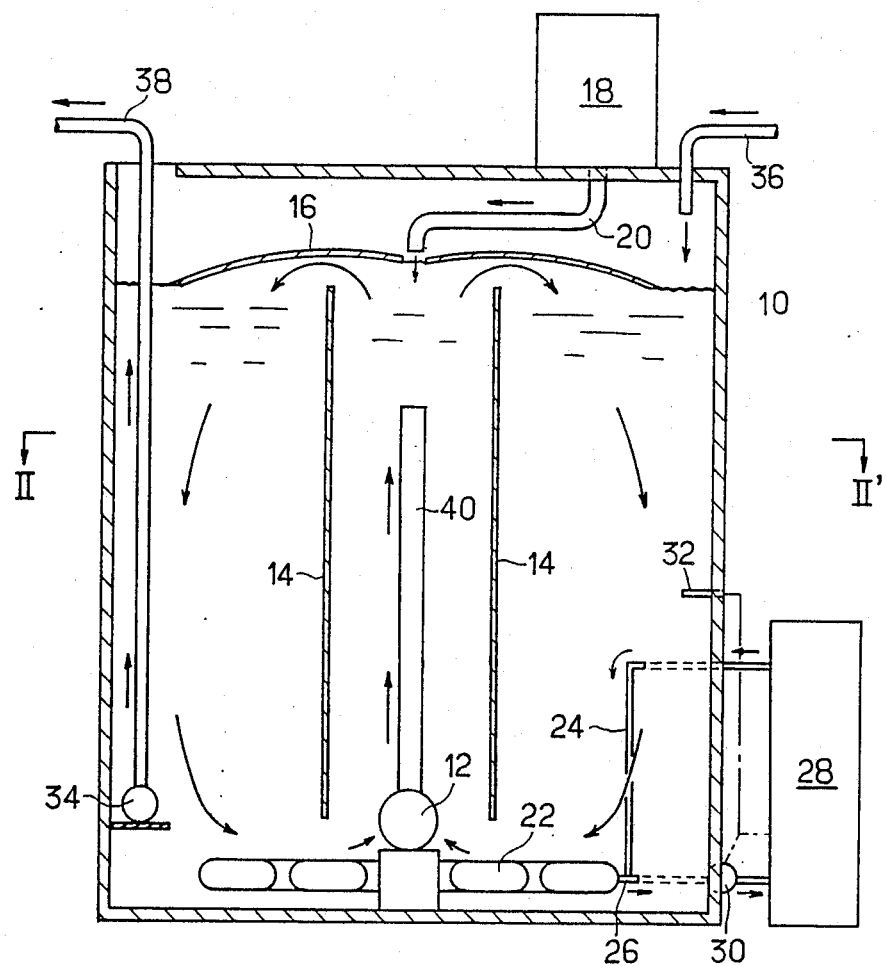
FIGS. 1 and 2 illustrate an embodiment according to a preferred embodiment of the present invention.
Figure 2:
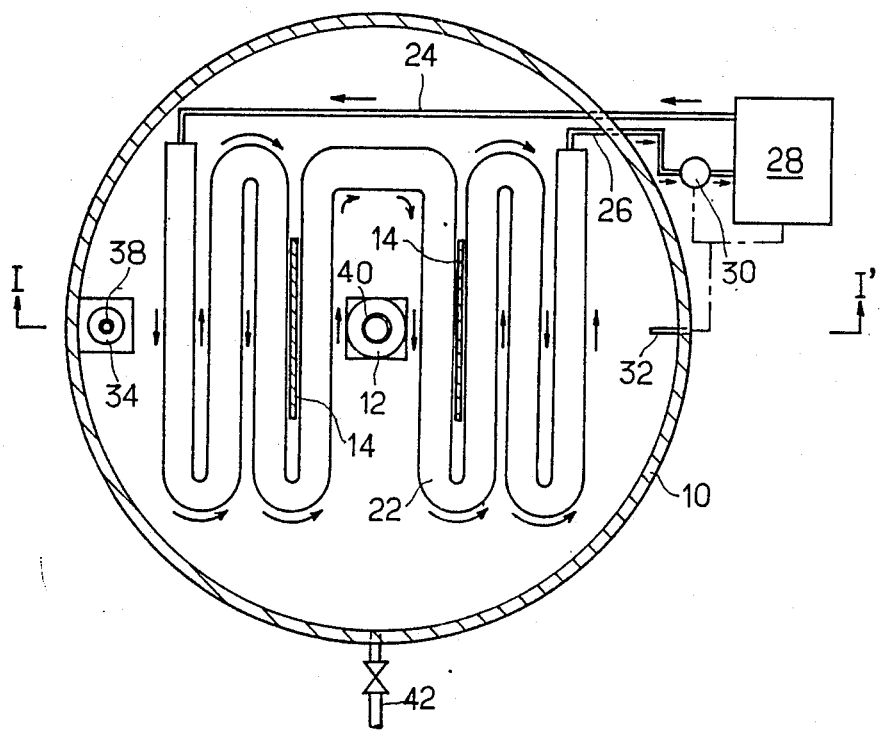

In FIGS. 1 and 2 illustrating partially sectional views of the sludge processing apparatus along the line I—I' in FIG. 2 and a sectional view thereof taken along the line II—II' in respectively, the sludge processing apparatus comprises a processing tank 10, a submersible pump 12 which is disposed in the center of bottom of the processing tank 10, a circulation guide plate comprising a pair of vertical plates 14, 14 both erected on the center of the processing tank 10 in such a manner as to face to each other and a horizontal disc 16 horizontally provided on the upper part of the processing tank 10, a chemical feeder comprising a chemical tank 18 disposed on the top cover of the processing tank 10, a chemical feed pipe 20 and an opening-and-closing device (not illustrated) of feed opening of the chemical tank, a hot water pipe 22 disposed near the bottom of the processing tank 10, a heating-and-circulating device comprising a heater 28 communicated with the hot water pipe 22 by way of pipe lines 24, 26 and a circulating pump 30 interposed in the pipe line 26, temperature control means comprising a temperature detector 32 inserted in the processing tank 10 through the side wall of the tank 10 and a temperature controller (not illustrated) to which the temperature detector 32 is connected by way of a lead wire, and a drain pump 34 disposed in the vicinity of a side wall of the processing tank 10.

In the processing tank 10, there is provided a sludge inflow pipe 36 which causes the sludge sent from the sewage water treating equipment by a vacuum device (not illustrated) to flow in the tank. Connected to the drain pump 34 is a drain pipe 38 for draining supernatant water produced after the sludge processing. A discharge pipe 40 is connected to the discharge opening of the submersible pump 12 disposed in the center of the bottom of the processing tank 10, and the discharge pipe 40 extends toward the liquid surface. A chemical selected for promoting activity of anaerobic bacteria which carries out anaerobic digestion of sludge is put in the chemical tank 18. An aqueous solution of a material containing natural emulsion surfactant and saponin extracted from plants is used as the chemical, for example. This chemical promotes the activity of bacteria and restrains generation of offensive odor. A quantity of hot water is sealed in the hot water pipe 22. The hot water is circulated through the pipe line 26, heater 28 and pipe line 24 by the circulating pump 30, and is heated when passing through the heater 28. In the drawing, numeral 42 denotes a drain pipe for draining insoluble inorganic materials.

Described hereinafter is an operation of the sludge processing apparatus of the above construction. Excess sludge generated in the seawage treating equipment is sent by the vacuum device, and flows into the processing tank 10 through the sludge inflow pipe 36. When the sludge is deposited in the processing tank 10, the submersible pump 12 is driven, whereby the sludge lying on the bottom of the tank is pumped into the pump and spouted upward to the liquid surface through the discharge pipe 40. The sludge spouted upward to the liquid surface comes in contact with the curved surface formed on the under side of the horizontal disc 16 and runs outwardly of the vertical plates 14, 14. Then, returning from the liquid surface portion to the bottom of the tank, the sludge is pumped into the submersible pump 12 again. The chemical preferably containing an emulsion surfactant and saponin is added to mix with the circulating sludge in this manner from the chemical tank 18 through the chemical feeding pipe 20, and the chemical is stirred and mixed with the sludge. Hot water sealed in the hot water pipe 22 is circfulated through the pipe line 26, heater 28 and pipe line 24 by the circulating pump 30 and is heated when passing through the heater 28. Thus, heat is given to the sludge circulating in the processing tank 10 by passing the hot water through the hot water pipe 22. In this step, the temperature of the sludge circulating in the processing tank 10 is detected by the temperature detector 32, and in accordance with a detection signal thereby, the circulating pump 30 and the heater 28 are controlled by the temperature controller so that the temperature of the sludge comes to an optimum temperature within a range of 29° to 45° C.

When the chemical is stirred and mixed with the sludge and the sludge temperature is adjusted to an optimum value, anaerobic bacteria living in the sludge are activated by synergistic function between the emulsion surfactant and saponin contained in the chemical, and the anaerobic digestion of sludge is speedily carried out by the vigorous activity of the anaerobic bacteria.

In this manner, the sludge is decomposed while discharging a large amount of methane gas in a short period. The sludge in the tank is completely decomposed after 8 to 10 days. In this process, generation of offensive odor in the period of acidity reduction is also restrained. As inorganic material precipitates on the bottom of the tank after the completion of a series of process, the supernatant water is discharged by the drain pump 34 by way of the drain pipe 38, and then the precipitated inorganic material is discharged through the discharge pipe 42. In this connection, since the chemical for activating the function of bacteria is still contained in the supernatant water, processing efficiency of the sewage treating equipment can be further improved by feeding this supernatant water back to the processing tank of the sewage treating equipment.

The sludge processing apparatus in this embodiment may be constructed as above described, but the scope of the invention is not limited to the foregoing description and related illustrations in the drawings, and various changes and modifications can be made without departing from the spirit of the invention. For example, the configuration of the circulation guide plate for circulating the sludge in the whole processing tank, place to dispose it, etc., are not intended to be restrictive.

What is claimed is:

1. A sludge processing apparatus, comprising: a processing tank, in which a quantity of sludge flowing in through a sludge inflow pipe is deposited and processed;
    submersible pump means, located centrally at the bottom in the processing tank, for taking in the sludge from the bottom of the processing tank and spouting it upward to the upper surface of the quantity of deposited sludge;
    a circulation guide plate, which circulates the sludge spouted upward by the submersible pump throughout the whole processing tank;
    chemical providing means, which feeds to the processing tank a quantity of a chemical for promoting activity of anaerobic bacteria carrying out anaerobic digestion of the sludge;
    heating medium means, providing a heating medium and circulating the same through a heating pipe disposed inside said processing tank to heat the sludge;
    temperature control means for controlling the temperature of the sludge in the processing tank to be within a predetermined temperature range; and
    drain pump means for pumping supernatant water that is left after processing of the sludge out of the processing tank through a drain pipe.

2. A sludge processing apparatus according to claim 1, wherein:
    said circulation guide plate comprises a pair of vertical plates disposed about the center of the processing tank to face to each other and a horizontal disc provided at an upper part of the processing tank.

3. The sludge processing apparatus according to claim 2, wherein:
    the heating pipe is disposed close to the bottom of the processing tank.

4. The sludge processing apparatus according to claim 2, comprising:
    means for draining a quantity of precipitated inorganic matter from said processing tank after processing of said quantity of sludge therein.

5. The sludge processing apparatus according to claim 1, wherein:
    the heating pipe is disposed close to the bottom of the processing tank.

6. The sludge processing apparatus according to claim 5, further comprising:
    drain pump means connected to said processing tank for removing a quantity of supernatant liquid after processing of said quantity of sludge and, after removal of a quantity of precipitated inorganic matter, selectively returning a portion of the supernatant water to the processing tank, to thereby return said chemical therein to promote activity of said anaerobic bacteria in processing of additional sludge brought thereto.

7. The sludge processing apparatus according to claim 1, further comprising:
    means for draining a quantity of precipitated inorganic matter from said processing tank after processing of said quantity of sludge therein.

8. The sludge processing apparatus according to claim 7, comprising:
    drain pump means connected to said processing tank for removing a quantity of supernatant liquid after processing of said quantity of sludge and, after removal of a quantity of precipitated inorganic matter, selectively returning a portion of the supernatant water to the processing tank, to thereby return said chemical therein to promote activity of said anaerobic bacteria in processing of additional sludge brought thereto.

9. The sludge processing apparatus according to claim 8, wherein:
    said circulation guide plate comprises a pair of vertical plates disposed about the center of the processing tank to face to each other and a horizontal disc provided at an upper part of the processing tank.

* * * * *